United States Patent
Rovaniemi

(10) Patent No.: US 10,426,669 B2
(45) Date of Patent: Oct. 1, 2019

(54) WOUND DRESSING AND A METHOD FOR MANUFACTURING A WOUND DRESSING

(71) Applicant: Absorbest AB, Kisa (SE)

(72) Inventor: Rolf Rovaniemi, Rimforsa (SE)

(73) Assignee: ABORBEST AB, Kisa (SE)

( * ) Notice: Subject to any disclaimer, the term of this patent is extended or adjusted under 35 U.S.C. 154(b) by 826 days.

(21) Appl. No.: 14/922,387

(22) Filed: Oct. 26, 2015

(65) Prior Publication Data
US 2016/0113818 A1 Apr. 28, 2016

(30) Foreign Application Priority Data
Oct. 27, 2014 (EP) .................................... 14190522

(51) Int. Cl.
*A61F 13/00* (2006.01)

(52) U.S. Cl.
CPC .. *A61F 13/00042* (2013.01); *A61F 13/00008* (2013.01); *A61F 13/00017* (2013.01); *A61F 13/00029* (2013.01); *A61F 13/00038* (2013.01); *A61F 13/00987* (2013.01); *A61F 2013/00119* (2013.01); *A61F 2013/00217* (2013.01); *A61F 2013/00327* (2013.01)

(58) Field of Classification Search
None
See application file for complete search history.

(56) References Cited

U.S. PATENT DOCUMENTS

| | | | | |
|---|---|---|---|---|
| 5,465,735 A | * | 11/1995 | Patel | A61F 13/022 128/888 |
| 5,728,084 A | * | 3/1998 | Palumbo | A61F 13/53704 604/368 |
| 6,169,223 B1 | * | 1/2001 | Mahr | A61F 13/00063 602/56 |

(Continued)

FOREIGN PATENT DOCUMENTS

| | | |
|---|---|---|
| EP | 2796119 A1 | 10/2014 |
| EP | 2851044 A1 | 3/2015 |

(Continued)

OTHER PUBLICATIONS

EP Appln. No. 14190522.4, European Extended Search Report, dated May 11, 2015, 4 pg.

*Primary Examiner* — Kim M Lewis
(74) *Attorney, Agent, or Firm* — Cuenot, Forsythe & Kim, LLC

(57) ABSTRACT

A wound dressing includes an absorbent core including a top surface and a bottom surface containing a superabsorbent substance, a facing layer including folded sections folded towards the top surface of the absorbent core, the facing layer entirely covering the bottom surface of the absorbent core, a backing layer, and a contact layer including folded sections covering parts of the folded sections of the facing layer, the contact layer folded to cover an entire area of the facing layer covering the bottom surface of the absorbent core and the contact layer is configured to be brought into contact with a wound. The facing layer and the backing layer (Continued)

form a pouch in which the absorbent core is located. The folded sections of the facing layer and the backing layer are joined together. The folded sections of the contact layer and the facing layer or the backing layer are joined together.

24 Claims, 3 Drawing Sheets

(56) References Cited

U.S. PATENT DOCUMENTS

| | | | |
|---|---|---|---|
| 6,221,460 B1 * | 4/2001 | Weber | A61F 13/4942 |
| | | | 428/131 |
| 2005/0143697 A1 | 6/2005 | Riesinger | |
| 2008/0312572 A1 | 12/2008 | Riesinger | |
| 2013/0012902 A1 | 1/2013 | Rovaniemi | |
| 2013/0261579 A1 * | 10/2013 | Hwang | A61L 15/58 |
| | | | 604/365 |
| 2015/0088085 A1 | 3/2015 | Rovaniemi | |

FOREIGN PATENT DOCUMENTS

| | | | | |
|---|---|---|---|---|
| WO | 2003094813 A1 | 11/2003 | | |
| WO | 2011104388 A1 | 9/2011 | | |
| WO | WO 2011104388 A1 * | 9/2011 | ....... | A61F 13/00012 |

\* cited by examiner

WOUND DRESSING AND A METHOD FOR MANUFACTURING A WOUND DRESSING

BACKGROUND

The present invention relates to wound dressings.

Wound dressings containing superabsorbent polymers in particular for application on heavily secreting wounds have been described in various forms in the prior art. For example the book "Modern Superabsorbent Polymer Technology" edited by Frederick L. Buchholz and Andrew T. Graham, published in 1998 by John Wiley & Sons, Inc., ISBN 0-471-19411-5 on page 251 discloses the usage of superabsorbent polymers for the design of effective wound dressings.

WO 03/094813 describes a wound dressing comprising a pouch, in which an absorbent core consisting of a non-woven material comprising superabsorbent polymers dispersed therein is located.

Typically, pouches of the prior art wound dressings containing a superabsorbent substance known from the prior art are formed by applying a seam between a facing layer and a backing layer. In order to be able to do so, the facing layer and the backing layer do extend beyond the absorbent core and are joined together, e.g. by using a glue, such that when viewed from the top the glued seam surrounds the area of the absorbent core.

Due to the seam surrounding the actual absorbent core, the known wound dressings tend to have edges, which do not have the desired softness of a medical product to be brought into contact with a patient's skin. Clinical use of such dressings has shown that due to the hard and stiff boundary area of the wound dressing skin irritations on the healthy skin surrounding the actual wound occur.

SUMMARY

A wound dressing includes an absorbent core including a top surface and a bottom surface containing a superabsorbent substance, a facing layer including two folded sections folded towards the top surface of the absorbent core, wherein the facing layer is folded to cover entirely the bottom surface of the absorbent core, a backing layer, and a contact layer including two folded sections covering parts of the folded sections of the facing layer, wherein the contact layer is folded to cover an entire area of the facing layer covering the bottom surface of the absorbent core and the contact layer is configured to be brought into contact with a wound. The facing layer and the backing layer are joined together by a seam, forming a pouch. The absorbent core is located in the pouch. The folded sections of the facing layer and the backing layer are joined together. The two folded sections of the contact layer and the facing layer or the backing layer are joined together by a seam.

A method for manufacturing a wound dressing includes providing an absorbent core including a top surface and a bottom surface containing a superabsorbent substance, providing a facing layer, locating the absorbent core on the facing layer, folding the facing layer so that the facing layer covers an entire bottom surface of the absorbent core and so that the facing layer includes two folded sections covering parts of the top surface of the absorbent core, providing a backing layer, joining together the facing layer and the backing layer by a seam so that the facing layer and the backing layer form a pouch, wherein the absorbent core is located in the pouch, wherein the seam is at least partly formed between the folded sections of the facing layer and the backing layer, providing a contact layer so that it covers the facing layer, folding the contact layer so that the contact layer including two folded sections covering parts of the folded sections of the facing layer, and joining together the folded sections of the contact layer and the facing layer or the backing layer by a seam.

DETAILED DESCRIPTION

Figure 1:
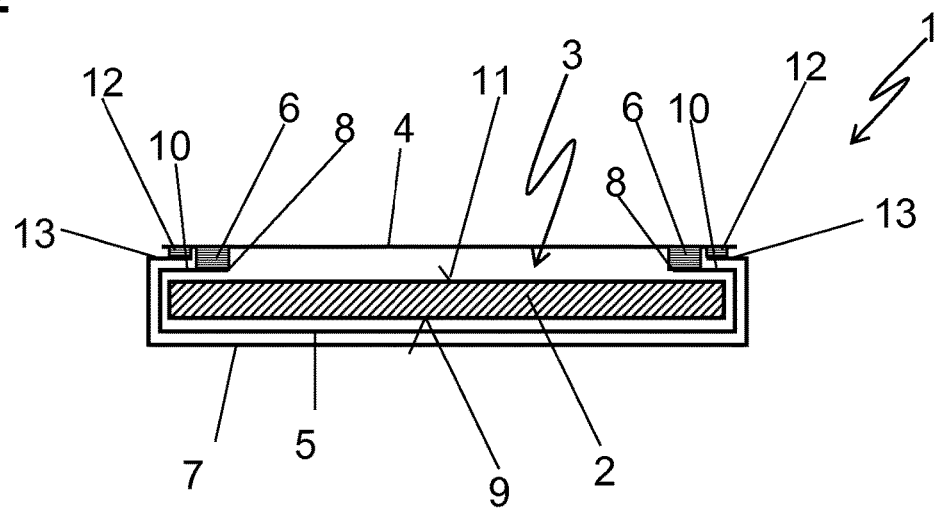
FIG. 1 shows a cross-sectional view of a wound dressing according to a first embodiment of the present invention.

It is an object of the present invention to provide a wound dressing reducing skin irritations around the wound and a method to manufacture such an improved wound dressing.

The present invention relates to a wound dressing comprising an absorbent core with a top surface and a bottom surface containing a superabsorbent substance, a facing layer, and a backing layer, wherein the facing layer and the backing layer are joined together by a seam forming a pouch, wherein the absorbent core is located in the pouch, wherein the facing layer is folded to cover the entire bottom surface of the absorbent core and comprising two folded sections folded towards the top surface of the absorbent core, wherein the folded sections of the facing layer and the backing layer are joined together.

The present invention further relates to a method for manufacturing a wound dressing comprising the following steps: providing an absorbent core with a top surface and a bottom surface containing a superabsorbent substance, providing a facing layer, locating the absorbent core on the facing layer, folding the facing layer such that the facing layer covers the entire bottom surface of the absorbent core and such that the facing layer comprises two folded sections covering parts of the top surface of the absorbent core, providing a backing layer, and joining together the facing layer and the backing layer by a seam such that the facing layer and the backing layer form a pouch, wherein the absorbent core is located in the pouch, wherein the seam is at least partly formed between the folded sections of the facing layer and the backing layer.

One requirement to a medical device as a wound dressing is that the medical device is designed such that no substances being foreign to the body to be treated can reach the wound and remain in the wound. A wound dressing will only be considered to be in conformity e.g. with the EU medical device directive 93/42/EEC of Jun. 14, 1993.

In particular designs wherein the absorbent core contains a superabsorbent substance in form of a granulate or particles, also called superabsorbent particles (SAP) in the terminology used in the present application, any leakage of SAP from the absorbent core into the wound has to be avoided. This is typically fulfilled by a pouch surrounding the absorbent core, wherein the pouch is formed by a facing layer and a backing layer joined together by a seam.

It is thus a further object of the present invention to provide a wound dressing which prevents substances foreign to the body to be treated from exiting the dressing and a method for manufacturing thereof.

When absorbing liquid, an absorbent core of a wound dressing tends to swell and thus starts applying forces, primarily tensile forces to the material surrounding the absorbent core and forming the pouch, wherein the core is located. Thus, in order to avoid any destructive effect to the facing layer and the backing layer by the swelling of the absorbent core, the facing layer as well as the backing layer forming the pouch surrounding the absorbent core must have a certain tensile strength. The same applies to the stability of the seam formed between the facing layer and the backing layer.

Frequently it turns out that the requirement of having a facing layer, i.e., the layer, which is facing towards a wound when the wound dressing is in use, comprising the necessary tensile strength in order to reliably avoid any leakage of substances from the pouch into the wound contradicts other requirements of a layer to be brought into contact with a wound.

It is thus another object of the present invention to provide a design of a wound dressing reliably avoiding leakage of SAP or any other substance being foreign to the body from the pouch, while simultaneously allowing to design the layer to be brought into contact with the wound matching other requirements.

At least one of the above objects is solved by a wound dressing comprising an absorbent core with a top surface and a bottom surface containing a superabsorbent substance, a facing layer, and a backing layer, wherein the facing layer and the backing layer are joined together by a seam forming a pouch, wherein the absorbent core is located in the pouch, wherein the facing layer is folded to cover the entire bottom surface of the absorbent core and comprising two folded sections folded towards the top surface of the absorbent core, wherein the folded sections of the facing layer and the backing layer are joined together, wherein the wound dressing further comprises a contact layer to be brought into contact with a wound, wherein the contact layer is folded to cover an entire area of the facing layer covering the bottom surface of the absorbent core and comprising two folded sections covering parts of the folded sections of the facing layer, and wherein the two folded sections of the contact layer and the facing layer or the backing layer are joined together by a seam.

It is the basic idea of the design of the wound dressing according to the present invention to provide a stable pouch containing the absorbent core, which could withstand any tensile forces applied by the absorbent core when swelling due to the absorption of liquid. Simultaneously there is a contact layer, whose properties can be designed independently from the requirement of having a reliable pouch in order to match other requirements of the wound dressing regarding the contact of the dressing with the wound.

In order to avoid any negative effects of the seams, the seams mounting or joining together the facing layer and the backing layer as well as the seams mounting together the facing layer and/or the backing layer and the contact layer have been transferred such that they don't get in direct contact with a patient's skin.

According to the present invention, at least two of the seams between the facing layer and the backing layer as well as between the contact layer and the facing layer or the backing layer have been transferred to a position such that they don't get in direct contact with a patient's skin. In an embodiment of the invention these are preferably the seams along the long sides of the wound dressing.

While transfer of the seams according to an embodiment of the present invention is at least provided for two sides of the wound dressing, there may be an embodiment, wherein the seams along all sides of the wound dressing, preferably four sides of the wound dressing, are such that they do not get in direct contact with the patient's skin. Thus in an embodiment of the present invention, the facing layer and the contact layer comprise four folded sections each.

A contact layer in the sense of the present application is the layer, which when the wound dressing is in use is brought into contact with the wound, i.e. is brought in engagement the wound surface.

In an embodiment of the present application, the contact layer has properties reducing its adhesion to a wound surface. This may in particular be achieved by a perforated plastic film. Such a plastic film in an embodiment of the present invention may be manufactured from anyone of the following materials or a combination thereof: polyethylene (PE), polyethylene terephthalate (PET), polyether, and polyamide.

In order to be permeable for fluid and exudate to reach the absorbent core in the pouch, the plastic film must either be perforated or apertured.

An example for perforated films are plastic films commercially available from Tredegar Corporation, North Chesterfield, USA, Pantex International, and RKWSE of Frankenthal, Germany. Examples for apertured films are commercially available from DelStar Technologies, Inc. of Middle Town, USA under the trade names Delnet, DelPore, Stratex and Naltex.

Other alternative materials for the contact layer in an embodiment include perforated or apertured films of silicone or non-woven materials or textile materials with a surface treatment of silicone, Teflon, wax or oil or other substances reducing adhesion to a wound surface.

These materials providing a non-sticking surface reducing the adhesion to a wound surface in an embodiment reduce pain implied to a patient, when the wound dressing is removed from the wound.

A perforated and apertured film of plastic material as the contact layer in an embodiment is two-dimensional. i.e., the film has a flat extended surface interrupted by through holes in order to be permeable for liquid.

However, in addition to the actual material properties of the surface of the material used, the adhesion of the contact layer to a wound surface may also or additionally be controlled, in particular be reduced, by providing the contact layer as a three-dimensional structure. A three-dimensional structure, e.g. a wavelike shape, reduces the overall area of the contact layer which is in direct contact with the wound surface and thus reduces the overall adhesion the contact layer experiences when in contact with the wound surface.

Such a three-dimensional structure may in an embodiment be formed by plastically deforming a two-dimensional plastic film, e.g., by embossing. Another example for an embodiment of a three-dimensional structure of a contact layer is a textile material, wherein due to the forming of meshes by the strands of the textile material the material layer inherently comprises a three-dimensional structure.

Typically, perforated or apertured films cannot reliably avoid leakage of SAP from a pouch, as when put under the tensile forces the pores or apertures will widen due to the fairly low tensile strength. It is thus an advantage of the wound dressing according to the present invention that the properties of the material used for the contact layer can be chosen independently from the requirements regarding the strength of the facing layer by providing the facing layer and the contact layer as distinct and separate layers.

Typically, the strength of embodiments of the contact layer having non-sticking surface properties and/or providing a good skin surface contact is rather low. Thus, in an embodiment according to the present invention the material of the facing layer has a higher tensile strength than the material of the contact layer.

In an embodiment of the wound dressing it is desirable once the dressing provides a one hundred percent contact with the surface of the wound. Expressed in other words, the wound dressing shall be in direct engagement with the wound surface all over the entire wound surface or at least approximate this state to a good extend. This provides a uniform flow of exudate from the entire wound surface into the absorbent core of the wound dressing. This in turn may reduce bacterial growth and thus maceration, which in particular occurs in areas, where there is no direct contact between the contact layer and the wound surface and thus the exudate is accumulated.

In order to provide a contact between the contact layer and the wound surface in an area as large as possible in an embodiment of the present invention, the contact layer has a higher elasticity than the material of the facing layer. This allows the facing layer to adopt its form or shape, such that it is in direct contact with an area of the wound surface being as large as possible.

In an embodiment the elasticity of the contact layer in a direction perpendicular to the bottom surface of the absorbent core (also denoted as the elasticity in the z-direction; z-elasticity) is higher than the elasticity of the facing layer in the direction perpendicular to the bottom surface of the absorbent core. The elasticity of the contact layer in the direction perpendicular to the bottom surface of the absorbent core in an embodiment not only depends on the material properties of the contact layer, but also on its thickness and/or its perforations/apertures and/or the shape of its three dimensional structure.

By joining together the folded sections of the contact layer and/or the folded sections of the facing layer and the backing layer any seams in engagement with the contact layer are transferred to a position avoiding any stiffening of the surface of the contact layer in areas to be brought into contact with the patient's skin.

In an embodiment, the backing layer, the facing layer, and the contact layer are arranged such that the folded sections of the contact layer at least partly extend between the backing layer and the folded sections of the facing layer. This allows fixation of the contact layer to the backing layer providing additional stability of the dressing.

In another embodiment according to the present invention, the folded sections of the contact layer are in engagement with an area of the folded sections of the facing layer which is smaller than the overall area of the folded sections of the facing layer and the backing layer is directly joined together with the area of the folded sections of the facing layer not in engagement with the folded sections of the contact layer. This embodiment allows a direct mounting of the backing layer to the facing layer providing a very stable pouch.

This in particular holds once the folded sections of the facing layer extend by approximately 10 mm to approximately 70 mm beyond the edge of the folded section of the contact layer.

In a further embodiment, the folded sections of the contact layer are smaller in size than the folded sections of the facing layer leaving an area of the facing layer exposed to be brought into direct contact via a seam with the backing layer.

In an embodiment of the present invention, the folded sections of the contact layer and the folded sections of the facing layer are joined together by a seam. In such an embodiment, the contact layer may in addition be joined together with the backing layer by a further seam, however it need not. Joining together the contact layer and the folded sections of the facing layer in order to fix the contact layer to the pouch provides significant advantages regarding the manufacturing process.

In an embodiment of the present invention, the facing layer and the contact layer are either not joined together at all by a direct seam between the two layers or the facing layer and the contact layer are exclusively joined together by a seam between the folded sections thereof. This avoids any stiffening of the contact layer at its surface to be brought into contact with the patient's skin.

There are further embodiments of the present invention, wherein the folded sections of the contact layer cover the entire folded sections of the facing layer, such that the folded sections of the contact layer are fully sandwiched between the folded sections of the facing layer and the backing layer.

A pouch formed by the facing layer and the backing layer in the sense of the present application is a hollow space containing the absorbent core and being sealed in that it avoids any leakage of substances of the absorbent core, in particular in an embodiment superabsorbent particles from the absorbent core, to the outside of the pouch.

This requires in an embodiment, that the pores, apertures or perforations of the facing layer and the backing layer are smaller than any possibly loose particle in the absorbent core, in particular than any superabsorbent particle, which in an embodiment may be contained in the absorbent core.

In an embodiment of the invention facing layer is arranged to accommodate any forces applied by a swelling of the absorbent core. Thus the risk of the contact layer being stretched and thus either becoming disrupted or the pore/openings/apertures being widened is drastically reduced. In these embodiments the facing layer and the backing layer in combination may be designed to avoid any leakage of particles from the pouch.

According to the present invention, the pouch containing the absorbent core is formed by a facing layer and a backing layer, wherein the facing layer and the backing layer are joined together.

By providing the facing layer and the backing layer as distinct and separate layers, their properties and functionalities can be individually designed as needed.

In an embodiment according to the present invention the facing layer is made of a material consisting of one selected of a group comprising a non-woven fabric, and a foam based on polyurethane (PU), silicone or a combination thereof.

In an embodiment, the facing layer comprises a non-woven fabric consisting of synthetic and/or cellulose fibers, wherein the fibers of the non-woven fabric are reoriented such that they predominantly extend in a direction perpendicular to the extension of the facing layer. Such a reorientation of the fibers in the non-woven fabric may be achieved by orienting the fibers during the fabrication process, in particular during spun lacing or needling.

In a particular embodiment of the present invention, the facing layer consists of a spunbond non-woven or a combination of a spunbond non-woven and a melt-blown non-woven, in particular SMS (spun-melt-spun), SMMS (spun-melt-melt-spun). In an embodiment, the facing layer of SMS or SMMS comprises an opened area for liquid to pass through in the range from 8 gsm to 20 gsm.

In an embodiment, the facing layer is a polypropylene spunbond non-woven comprising an opened area for liquid to pass through in the range from 10 gsm to 25 gsm.

In a further embodiment, the facing layer in its unwetted state comprises a weight in a range from 12 g/m2 to 40 g/m2, preferably in a range from 18 g/m2 to 25 g/m2.

It may be further useful if in an embodiment the facing layer comprises a hydrophobic or hydrophilic and/or bactericidal or bacteriostatic agent or a combination thereof.

In an embodiment of the present invention the elongation of the facing layer in a direction parallel to the bottom surface of the absorbent core is in a range from approximately 40% to approximately 100%.

In an embodiment of the present invention, the backing layer serves as a clothing protection. In an embodiment, the backing layer is thus advantageously made of a breathable non-woven fabric or a perforated film enabling a breathing of the wound, but preventing wound exudates from exiting the wound dressing and contaminating a patient's clothing.

The backing layer may form the outermost layer of the wound dressing at the side facing away from the wound, which if applicable is brought into contact with the patient's clothing. However, there may be embodiments, wherein there are further layers on top of the backing layer, i.e. between the backing layer and the patient's clothing, providing additional functionalities for the wound dressing. One such functionality for example could be to provide an adhesive in order to permanently fix the dressing to the skin (border dressing).

In an embodiment of the present invention, the material of the backing layer is selected of a group comprising a spun bond non-woven, SMMS, SMSMS, a laminate of a non-woven material and a breathable film, like BTBS, and a breathable film, e.g. a polyurethane film.

The absorbent core according to the present invention may be any structure of material comprising a superabsorbent substance. Superabsorbent substances in the sense of the present application are materials that have the ability to absorb and retain large volumes of water and aqueous solutions. Superabsorbent substances falling into this category are for example modified starch, polymer-like polyvinyl alcohol (PVA), polyethylene oxide (PEO) which are all hydrophilic and have a high affinity to water. When chemically or physically cross-linked, these polymers are water-swellable but not water-soluble. The afore-mentioned superabsorbents have been known for a long time.

The superabsorbent can alternatively be a particle, granulate, fiber or have any other form.

In a particular embodiment of the present invention, the superabsorbent substance is a superabsorbent polymer (SAP) in the form of (granular) particles. In particular SAP may in an embodiment be made from polymerization of acrylic acids blended with sodium hydroxide in the presence of an initiator to form a poly-acrylic acid sodium salt (sometimes referred to as a sodium poly-acrylate).

In an embodiment, the core containing a SAP in the form of particles comprises at least two carrier layers. In particular the carrier layers can be at least two non-woven fabric layers or at least two layers of tissue paper or at least two cellulose layers. For fabrication the superabsorbent particles are put on the first carrier layer, then the second carrier layer is put on top and the two carrier layers are consolidated providing a matrix carrying the superabsorbent particles between the two carrier layers.

In a particular embodiment, the two carrier layers are made of a material selected of the group comprising cellulose, fluff, tissue, textile, spunlaced material and spun bond material.

In an embodiment, wherein the material of the carrier layers is a spunlaced material, it contains preferably 100% of Rayon fibers or a mixture of Rayon fibers and a smaller content from 5 to 30% of polyester fibers to give the required elasticity when wet.

A non-woven fabric in the sense of the present application is a material made of at least one layer of long fibers which have been formed to a web and in the next step consolidated. In particular, the consolidation of a non-woven fabric may be achieved by friction and/or cohesion and/or adhesion, for example by needling, felting, spun lasing, melting or heat embossing.

Once compared to a tissue paper, a material will be considered a non-woven fabric in the sense of the present application if more than 50% of the mass of its fiber components consist of fibers having a ratio of length to their diameter of more than 300. Alternatively, the material will be considered a non-woven fabric in the sense of the present application if this condition is not fulfilled, but if more than 30% of the mass of its fiber components consist of fibers having a ratio of their length to their diameter of more than 300 and its density is lower than 0.4 g/cm3. This definition corresponds to EN 29 092.

While an absorbent core according to any of the embodiment described above may be advantageous, it is not excluded to design absorbent cores using different material combinations, as long as the absorbent core contains a superabsorbent substance.

The absorbent core as used for the present invention extracts and stores any exudates from a wound, to which the wound dressing is applied to. In order to avoid a direct contact between the absorbent core and the wound surface, the wound dressing comprises a pouch, wherein the core is enclosed in the pouch.

In an embodiment of the invention, the absorbent core or the facing layer or any of the functional layers of the wound dressing may comprise a substance supporting wound healing, like for example *arnica montana*, polyhexanide (PHMB), polyhexamethylen, collagen or chitosan, which are released when the wound dressing is applied to a patient's wound.

The facing layer, the backing layer, and/or the contact layer may be joined together in different ways by a seam. In an embodiment of the invention the seam is formed by gluing, welding or ultrasound welding.

In a particular embodiment of the present invention, a seam is formed by gluing together two or more layers of the wound dressing. In an embodiment the glue is a polyolefin based hot melt providing a soft feeling even after gluing.

At least one of the above objects is also solved by a method for manufacturing a wound dressing comprising the steps: Providing an absorbent core of the top surface and the bottom surface containing a superabsorbent substance, providing a facing layer, locating the absorbent core on the facing layer, folding the facing layer such that the facing layer covers the entire bottom surface of the absorbent core and such that the facing layer comprises two folded sections folded towards the top surface of the absorbent core, providing a backing layer, and joining together the facing layer and the backing layer to form a pouch, wherein the absorbent core is located in the pouch, wherein the seam is at least partly formed between the folded sections of the facing layer and the backing layer, and providing a contact layer such that it covers the facing layer, folding the contact layer such that the contact layer comprises two folded sections covering parts of the folded sections of the facing layer, and joining together the folded sections of the contact layer and the facing layer or the backing layer by a seam.

In an embodiment of the present invention the following steps are carried out in the order given: Joining the contact layer and the facing layer together by two seams, preferably running parallel to each other, locating the absorbent core on the facing layer, wherein the bottom surface of the absorbent core faces the facing layer, folding the facing layer and the contact layer along two edges of the absorbent core such that the folded sections of the facing layer, the folded sections of the contact layer and the two seams between the contact layer and the facing layer are folded towards the top surface of the absorbent core and joining together the facing layer and the backing layer by forming a seam between the folded sections of the facing layer and the backing layer.

FIG. 1 shows a cross-sectional view of the first embodiment of a wound dressing 1 having a tubular design according to the present invention. The wound dressing 1 comprises an absorbent core 2.

Figure 2:
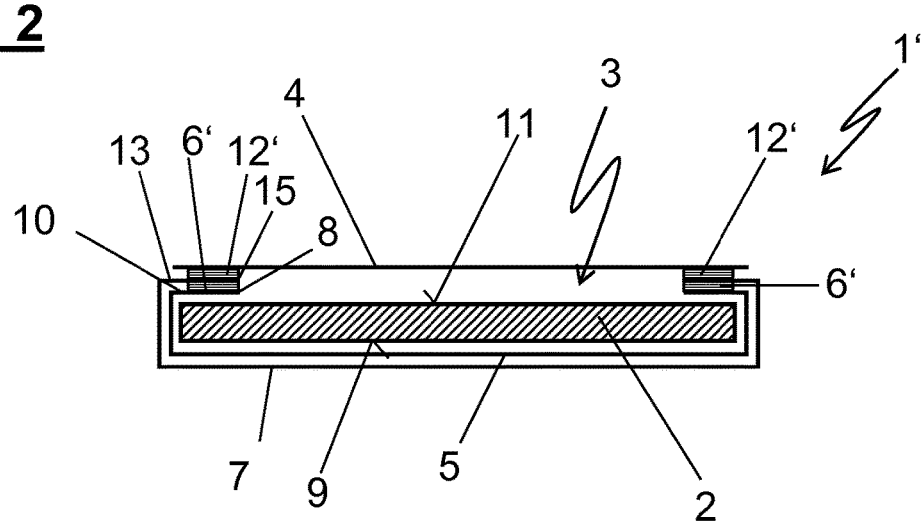
FIG. 2 shows a cross-sectional view of a wound dressing according to a second embodiment of the present invention.
Figure 3:
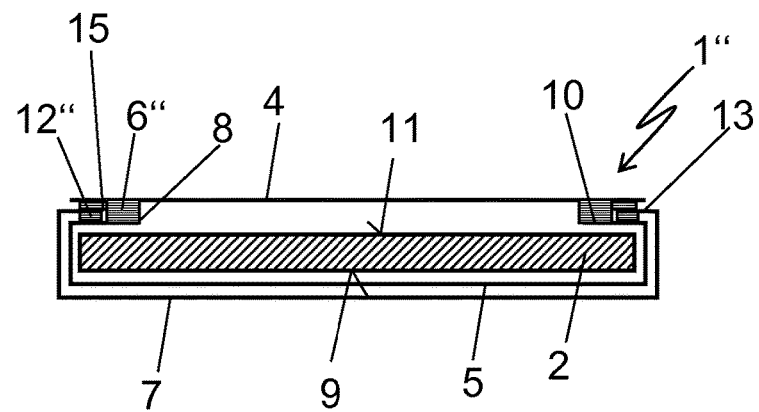
FIG. 3 shows a cross-sectional view of yet another embodiment of a wound dressing according to the present invention.
Figure 4:
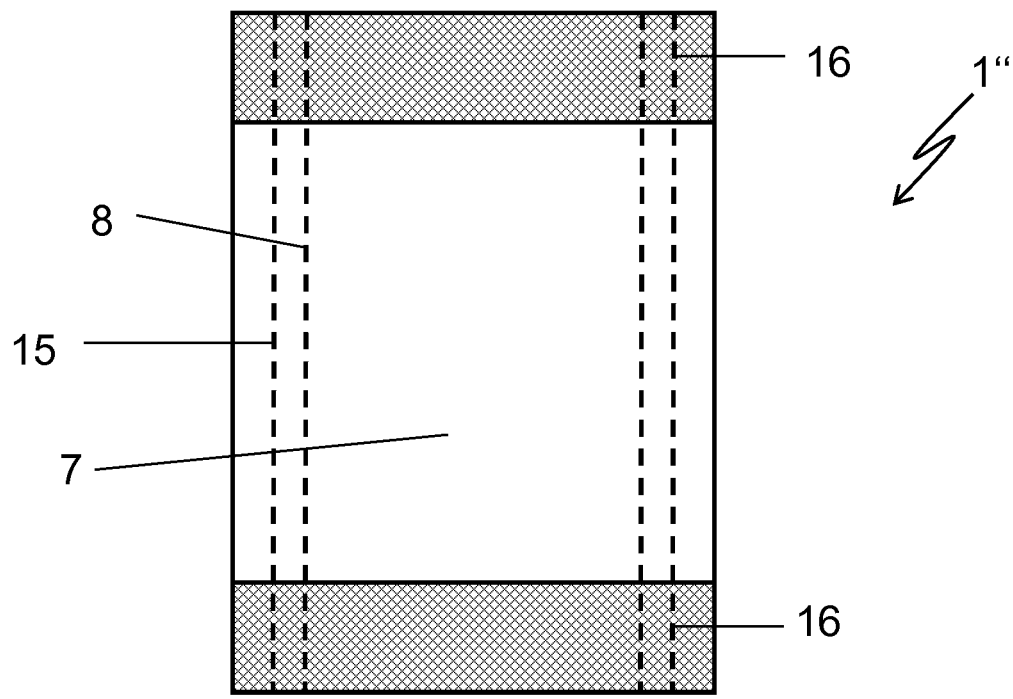
FIG. 4 shows a schematic bottom view of the wound dressing of FIG. 3.

In this particular embodiment, but also in the further embodiments according to FIGS. 2 to 4, the absorbent core 2 contains a SAP in the form of granular particles. The absorbent core 2 is formed by two layers of a non-woven fabric (not depicted in the figures), wherein the non-woven fabric is a spun laced material containing 25% polyester and 75% rayon fiber. This forms a material having high elasticity. For fabrication of the absorbent core 2 the superabsorbent particles are dispersed on top of a first layer of the non-woven fabric. Then the second layer of the non-woven fabric is put on top and the two layers are consolidated providing a matrix carrying the superabsorbent particles in between the two layers. These two layers are considered the carrier layers of the absorbent core 2 in the sense of the present application. As an example for an alternative design of the absorbent core the spunbond material as described above could be replaced by two sheets or carrier layers of cellulose or tissue paper.

In order to be used as a medical device the wound dressing 1 must be designed such that any substances being part of the wound dressing 1 cannot be separated from the dressing and enter the wound as a substance being foreign to the body. In order to reliably avoid that e.g. SAP particles from the absorbent core 2 exit the dressing 1 and enter the wound, the absorbent core 2 is contained in a pouch 3 formed by a backing layer 4 and a facing layer 5. The pouch 3 formed by the backing layer 4 and the facing layer 5 is tight in the sense that all its openings or apertures are smaller than those particles which can be expected to become lose and move freely within the pouch 3.

This is an important design requirement in particular for the facing layer 5 as the facing layer 5 at the same must be permeable for liquid exuding from a wound in order to be absorbed by the absorbent core 2.

When absorbing liquid, in particular exudate from a wound, the absorbent core 2 starts swelling, i.e. increases in volume. This increase in volume applies forces to the layers 4, 5 forming the pouch 3. In order to still provide its function as a confinement in particular for SAP contained in the core under swelling conditions of the core 2, the material of the facing layer 5 and of the backing layer 4 must be chosen to withstand any forces applied by the swelling core 2. This means that the material in particular shall not be disrupted and the pores (or openings or apertures) in particular of the facing layer 5 are not widened to an extent that particles may fall out of the pouch 3.

The requirement of providing a reliable confinement not only influences the design and choice of the material for the backing layer 4 as well as the facing layer 5, but also requires that all seams 6 used to join or connect the layers of the pouch to form a close shell or cover must be chosen and applied appropriately.

For the embodiments depicted in FIGS. 1 to 4, all seams 6, 6', 6'', 12, 12', 12'' are formed by gluing together the respective layers of the wound dressing. In the particular embodiments according to FIGS. 1 to 4, the glue used to form the respective seams is a polyolefin based hot melt providing a soft feeling even when the gluing process is finished, i.e. the glue is bound.

Requirements for a layer of the wound dressing to be brought into direct contact with the wound surface are in particular that this layer, which is considered a contact layer in the sense of the present application, is highly flexible, i.e. has a high elasticity in a direction perpendicular to the bottom surface 9 of the absorbent core 2, and has non-sticking properties when considering engagement of the contact layer with the wound surface. A direct contact of the contact layer with the wound surface enables a steady flow of exudate from the wound surface into the wound dressing 1. If however islands are formed on the wound surface, wherein the contact layer is not in contact with the wound surface in these islands the flow of exudate from the wound surface into the wound dressing 1 is reduced forming a starting point for bacteria growth. Full contact of the entire surface area of a wound surface can be achieved by designing the contact layer of a wound dressing such that it has a high elasticity in a direction perpendicular to the bottom surface 9 of the absorbent core 2.

Once the surface of the contact layer is such it has a reduced adhesion to the wound surface, pain imposed for the patient when removing the wound dressing from the wound is reduced.

It is apparent that the requirements of the contact layer 7 of the wound dressing might contradict the confinement requirement of the facing layer 5 as described above.

In order to resolve this contradiction, the wound dressings according to the present invention and as in particular depicted in FIGS. 1 to 4 the facing layer 5 forming part of the pouch 3 confining the absorbent core 2 and the contact layer 7 to be brought into engagement with the wound surface are designed as distinct and separate layers. This allows for an optimization of the facing layer 5 and the contact layer 7 to maximize their matching to respect to the requirements.

In the embodiments according to FIGS. 1 to 4 the contact layer 7 is a polyethylene (PE) film which is perforated in order to enable an effective flow of exudate through the film and which is embossed such that it provides a three-dimensional structure. The overall contact area between the contact layer 7 and a wound surface depends on the elasticity of the contact layer 7 in the direction perpendicular to the bottom surface 9 of the absorbent core 2.

This contact layer 7 has a low elasticity as well as a low adhesion to the surface of the wound. However, its tensile strength is far below the tensile strength of the facing layer 5. Thus, once the contact layer 7 would be used without the facing layer to form part of the pouch 3 containing the absorbent core 2 it would be stretched by the forces applied due to the swelling of the absorbent core 2 such that it either becomes disrupted or its perforations are stretched in a way that the confinement requirement is no longer fulfilled.

It has turned out that joining together two layers of the wound dressing, in particular by using a glue tends to stiffen the individual layers in those areas, wherein the seams are formed. These stiffened parts of the layers when brought into contact with the skin lead to skin irritations and a reduced healing.

Thus, according to the present invention and as depicted in all embodiments according to FIGS. 1 to 4 the seams 6, 6', 6", 12, 12', 12" have been transferred to an area of the wound dressing 1, 1', 1" wherein during appropriate use of the dressings 1, 1', 1" they do neither get in touch with the wound surface not with the healthy skin surrounding the wound.

This has been achieved by folding the facing layer 5 parallel to its edges 8 such that the facing layer 5 covers the entire bottom surface 9 of the absorbent core 2 and the folded sections 10 of the facing layer 5 are folded towards the top surface 11 of the absorbent core 2. In the particular embodiments according to FIGS. 1 to 4 the folded sections 10 do extend to cover parts of the top surface 11 of the absorbent core 2. However, this needn't necessarily be the case once the absorbent core 2 is substantially smaller than the area of the pouch formed by the facing layer 5 and the backing layer 4.

In order not to contradict the efforts made with respect to the seams 6, 6', 6" joining together the backing layer 4 and the facing layer 5, the seams 12, 12', 12" which mount the contact layer 7 to the rest of the structure of the absorbent core 1, 1', 1" have also been transferred to a location at the wound dressing, where they will not get into direct contact with the patient's skin.

In order to achieve this, the contact layer 7 has been folded, too. The contact layer 7 thus covers the entire facing layer 5 in the area of the facing layer 5 in engagement with or extending parallel to the bottom surface 9 of the absorbent core 2. Two folded sections 13 of the contact layer 7 have been folded towards the top surface 11 of the absorbent core 2, such that they extend in parallel to the folded sections 10 of the facing layer 5. Thus the folded sections 10 of the facing layer 5 and the folded sections 13 of the contact layer 7 do have an overlap.

In the particular embodiment of FIG. 1 the contact layer 7 is joined together with the backing layer 4 by the seams 12. This particular embodiment has the advantage that the seams 6, 12 (e.g., glue lines) can be applied simultaneously and then the backing layer is put on top and is pressed by a nip bar towards the contact layer 7 and the facing layer 5.

In the embodiments depicted in FIGS. 1 to 4 the backing layer 4 is provided by a laminate of a non-woven fabric and a breathable film called BTBS, which not only avoids exudate from exiting the wound dressing 1 and contaminating the patient's clothing, but also allows for a breathing of the wound dressing and thus the wound. This type of backing layer is also softer when compared to existing materials frequently used for the design of wound dressings.

FIG. 2 shows an alternative embodiment, wherein identical materials have been chosen in order to form the absorbent core 2, the backing layer 4, the facing layer 5, the contact layer 7 as well as the seams 6', 12'. However, joining the backing layer 4, the facing layer 5 as well as the contact layer 7 together has been changed when compared to the embodiment of FIG. 1.

In this particular embodiment of FIG. 2 the folded sections 10, 13 of the facing layer 5 and the contact layer 7 do have a full overlap such that in the area of the seams 6', 12' a sandwich structure between the three layers 4, 5, 7 is formed. The folded sections 13 of the contact layer 7 extend between the folded sections 10 of the facing layer 5 and the backing layer 4. A first seam 6' is formed between the contact layer 7 and the facing layer 5 and a second seam 12' is formed between the facing layer 7 and the backing layer 4.

FIGS. 3 and 4 show yet another embodiment, wherein again the materials chosen to form the backing layer 4, the absorbent core 2, the facing layer 5, the glue for the seams 6", 12" as well as the contact layer 7 are identical to the embodiments as depicted in FIGS. 1 and 2.

In this embodiment the facing layer 5 and the contact layer 7 are joined together by a seam 12" between their folded sections 10, 13 in order to attach the contact layer 7 to the structure of the wound dressing 1". However, the contact layer 7 is arranged and folded such that its folded sections 13 only cover a part of the area of the folded sections 10 of the facing layer 5. This leaves an area of the folded sections 10 of the facing layer 5 exposed to be glued by a second glue line 6" directly to the backing layer 4. The same glue line 6" is however also used to join together the backing layer 4 and the contact layer 7. This way any tensile forces applied to the facing layer 5 are directly transferred to the backing layer 4.

FIG. 4 shows a schematic bottom view of the dressing 1" of FIG. 3. I.e. it is a view onto the contact layer 7 from a direction denoted by the arrow 14 in FIG. 3. The edges 8, 15 of the folded sections 10, 13 of the facing layer 5 and the contact layer 7, respectively are denoted as dotted line in FIG. 4.

In FIG. 4 also those glue lines 16 in a transverse direction are depicted, which close the pouch in a direction perpendicular to the extension of the glue lines 6", 12". This sealing of the wound dressing 1" at its ends, i.e. perpendicular to a running direction of the material in the manufacturing process is carried out between the different layers 4, 5, 7 of the wound dressing 1" without folding the respective sections of the layers 4, 5, 7. However, embodiments are feasible, wherein also the glue lines 16 in the perpendicular direction are formed between folded sections of the facing layer 5, the contact layer 7 and the backing layer 4.

FIGS. 5 to 9 schematically demonstrate the manufacturing process for a wound dressing 1" of the embodiment depicted in FIGS. 3 and 4.

Figure 5:
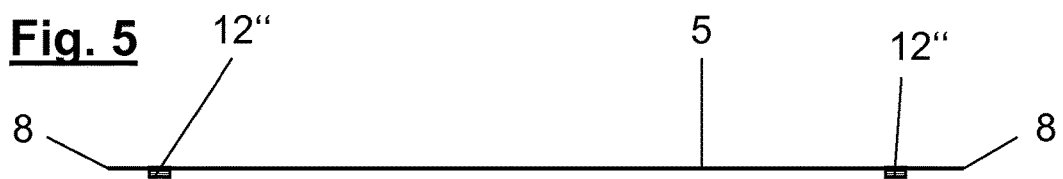
FIGS. 5 to 9 show individual steps in a process to manufacture the wound dressing of FIGS. 3 and 4.

In a first step depicted in FIG. 5 the facing layer 5 is provided and the glue lines 12" are applied. These glue lines 12" extend essentially parallel to the edges 8 of the facing layer 5, wherein in the manufacturing process the extension of the edges 8 as well as the glue lines 12" is parallel to the running direction of an endless material sheets used as the facing layer, backing layer and contact layer.

Figure 6:
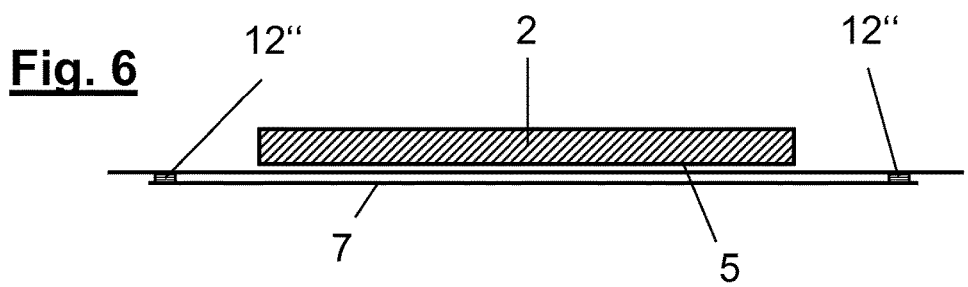
Figure 7:
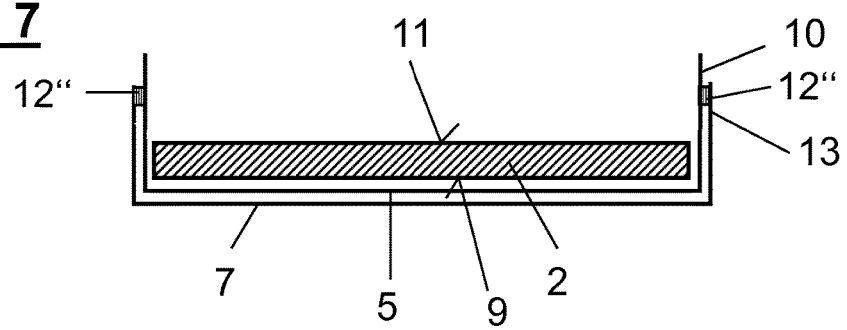

In FIG. 6 the absorbent core 2 is put on top of the facing layer 5 and the contact layer 7 is glued to the facing layer 5 using the glue lines 12". In FIG. 7 the facing layer 5 as well as the contact layer 7 are folded towards the top surface 11 of the absorbent core 2 forming two folded sections 10, 12 for each layer extending on top of the top surface 11 of the absorbent core 2.

Figure 8:
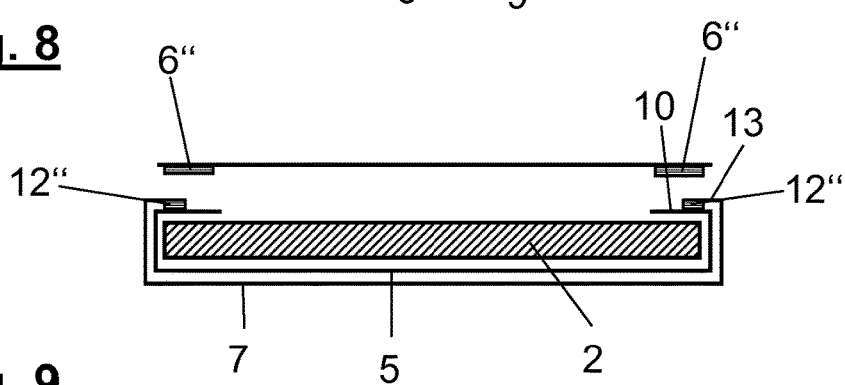

In FIG. 8 glue line 6" is applied on the backing layer 4.

Figure 9:
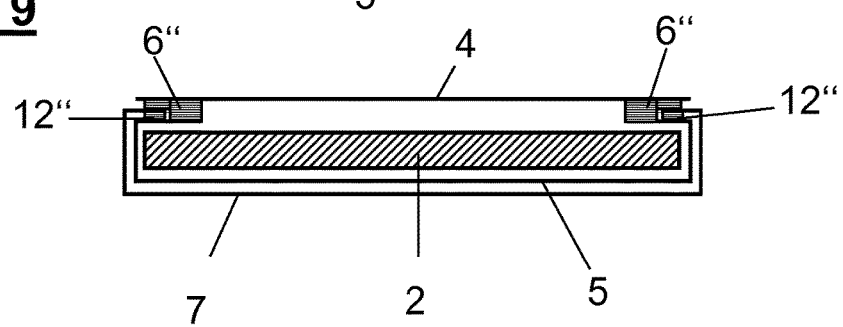

Finally in FIG. 9 the backing layer 4 is applied by the glue line 6" to the contact layer 7 as well as the facing layer 5.

In the figures similar elements have been identified by identical reference numbers. Regarding the purposes of the original disclosure, it is pointed out that all features which are apparent for a person skilled in the art from the present description, the figures and the claims, even if they have only been described with further features, could be combined on their own or together with all the combinations of the features disclosed herein if not excluded explicitly or technically impossible. It will be readily apparent to one skilled in the art that various combinations of the features described in the detailed description are possible, and the present arrangements are not limited in this regard.

What is claimed is:

1. A wound dressing comprising:
   an absorbent core comprising a top surface and a bottom surface containing a superabsorbent substance;
   a facing layer comprising two folded sections folded towards the top surface of the absorbent core, wherein the facing layer is folded to cover entirely the bottom surface of the absorbent core;
   a backing layer; and
   a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;
   wherein the facing layer and the backing layer are joined together by a seam, forming a pouch;
   wherein the absorbent core is located in the pouch;
   wherein the two folded sections of the facing layer and the backing layer are joined together;
   wherein the two folded sections of the contact layer and the facing layer or the backing layer are joined together by a seam;
   wherein the backing layer, the facing layer, and the contact layer are arranged so that the two folded sections of the contact layer at least partly extend between the backing layer and the two folded sections of the facing layer.

2. The wound dressing of claim 1, wherein the two folded sections of the contact layer and the two folded sections of the facing layer are joined together by a seam.

3. The wound dressing of claim 1, wherein the facing layer and the contact layer are exclusively joined together by a first seam between a first of the two folded sections of the facing layer and a first of the two folded sections of the contact layer and a second seam between a second of the two folded sections of the facing layer and a second of the two folded sections of the contact layer.

4. The wound dressing of claim 1, wherein the backing layer and the two folded sections of the facing layer and the two folded sections of the contact layer are joined together by a seam.

5. The wound dressing of claim 1, wherein the two folded sections of the contact layer engage an area of the two folded sections of the facing layer which is smaller than an overall area of the two folded sections of the facing layer, and the backing layer is directly joined together with the area of the two folded sections of the facing layer not in engagement with the two folded sections of the contact layer.

6. The wound dressing of claim 1, wherein the contact layer is not joined together with the facing layer, and wherein the contact layer is joined together with the backing layer by a seam.

7. The wound dressing of claim 1, wherein the two folded sections of the facing layer and the two folded sections of the contact layer extend along a long side of the wound dressing.

8. The wound dressing of claim 1, wherein a material of the facing layer has a higher tensile strength than a material of the contact layer.

9. The wound dressing of claim 1, wherein a material of the contact layer has a higher elasticity than a material of the facing layer, wherein the contact layer has a higher elasticity than the facing layer in a direction perpendicular to the bottom surface of the absorbent core.

10. The wound dressing of claim 1, wherein a material of the contact layer has properties reducing its adhesion to a wound surface.

11. The wound dressing of claim 1, wherein a material of the contact layer is a perforated plastic film.

12. The wound dressing of claim 1, wherein a material of the contact layer is a three-dimensional structure formed by embossing of a plastic film.

13. A method for manufacturing a wound dressing comprising:
   providing an absorbent core comprising a top surface and a bottom surface containing a superabsorbent substance;
   providing a facing layer;
   locating the absorbent core on the facing layer;
   folding the facing layer so that the facing layer covers an entire bottom surface of the absorbent core and so that the facing layer comprises two folded sections covering parts of the top surface of the absorbent core;
   providing a backing layer;
   joining together the facing layer and the backing layer by a seam so that the facing layer and the backing layer form a pouch, wherein the absorbent core is located in the pouch, wherein the seam is at least partly formed between the two folded sections of the facing layer and the backing layer;
   providing a contact layer so that it covers the facing layer;
   folding the contact layer so that the contact layer comprises two folded sections covering parts of the two folded sections of the facing layer;
   arranging the backing layer, the facing layer, and the contact layer so that the two folded sections of the contact layer at least partly extend between the backing layer and the two folded sections of the facing layer; and
   joining together the two folded sections of the contact layer and the facing layer or the backing layer by a seam.

14. The method of claim 13, wherein:
   joining the contact layer and the facing layer together by the seam is performed prior to locating the absorbent core on the facing layer, wherein the bottom surface of the absorbent core faces the facing layer;
   locating the absorbent core on the facing layer is performed prior to folding the facing layer and the contact layer along two edges of the absorbent core wherein the two folded sections of the facing layer cover part of the top surface of the absorbent core and wherein the seam between the facing layer and the contact layer is located on top of the top surface of the absorbent core; and
   folding the facing layer and the contact layer along two edges of the absorbent core is performed prior to joining together the facing layer and the backing layer by forming a seam between the two folded sections of the facing layer and the backing layer.

15. A wound dressing comprising:
   an absorbent core comprising a top surface and a bottom surface containing a superabsorbent substance;
   a facing layer comprising two folded sections folded towards the top surface of the absorbent core, wherein the facing layer is folded to cover entirely the bottom surface of the absorbent core;

a backing layer; and a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;

wherein the facing layer and the backing layer are joined together by a seam, forming a pouch;

wherein the absorbent core is located in the pouch;

wherein the two folded sections of the facing layer and the backing layer are joined together;

wherein the two folded sections of the contact layer and the facing layer or the backing layer are joined together by a seam;

wherein the facing layer and the contact layer are exclusively joined together by a first seam between a first of the two folded sections of the facing layer and a first of the two folded sections of the contact layer and a second seam between a second of the two folded sections of the facing layer and a second of the two folded sections of the contact layer.

16. A wound dressing comprising:

an absorbent core comprising a top surface and a bottom surface containing a superabsorbent substance;

a facing layer comprising two folded sections folded towards the top surface of the absorbent core, wherein the facing layer is folded to cover entirely the bottom surface of the absorbent core;

a backing layer; and a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;

wherein the facing layer and the backing layer are joined together by a seam, forming a pouch;

wherein the absorbent core is located in the pouch;

wherein the two folded sections of the facing layer and the backing layer are joined together;

wherein the two folded sections of the contact layer and the facing layer or the backing layer are joined together by a seam;

wherein the backing layer and the two folded sections of the facing layer and the two folded sections of the contact layer are joined together by a seam.

17. A wound dressing comprising:

an absorbent core comprising a top surface and a bottom surface containing a superabsorbent substance;

a facing layer comprising two folded sections folded towards the top surface of the absorbent core, wherein the facing layer is folded to cover entirely the bottom surface of the absorbent core;

a backing layer; and a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;

wherein the facing layer and the backing layer are joined together by a seam, forming a pouch;

wherein the absorbent core is located in the pouch;

wherein the two folded sections of the facing layer and the backing layer are joined together;

wherein the two folded sections of the contact layer and the facing layer or the backing layer are joined together by a seam;

wherein the two folded sections of the contact layer engage an area of the two folded sections of the facing layer which is smaller than an overall area of the two folded sections of the facing layer, and the backing layer is directly joined together with the area of the two folded sections of the facing layer not in engagement with the two folded sections of the contact layer.

18. A wound dressing comprising:

an absorbent core comprising a top surface and a bottom surface containing a superabsorbent substance;

a facing layer comprising two folded sections folded towards the top surface of the absorbent core, wherein the facing layer is folded to cover entirely the bottom surface of the absorbent core;

a backing layer; and a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;

wherein the facing layer and the backing layer are joined together by a seam, forming a pouch;

wherein the absorbent core is located in the pouch;

wherein the two folded sections of the facing layer and the backing layer are joined together;

wherein the two folded sections of the contact layer and the facing layer or the backing layer are joined together by a seam;

wherein the contact layer is not joined together with the facing layer, and wherein the contact layer is joined together with the backing layer by a seam.

19. A wound dressing comprising:

an absorbent core comprising a top surface and a bottom surface containing a superabsorbent substance;

a facing layer comprising two folded sections folded towards the top surface of the absorbent core, wherein the facing layer is folded to cover entirely the bottom surface of the absorbent core;

a backing layer; and a contact layer comprising two folded sections covering parts of the two folded sections of the facing layer, wherein the contact layer is folded to cover an entire area of the facing layer covering the bottom surface of the absorbent core and the contact layer is configured to be brought into contact with a wound;

wherein the facing layer and the backing layer are joined together by a seam, forming a pouch;

wherein the absorbent core is located in the pouch;

wherein the two folded sections of the facing layer and the backing layer are joined together;

wherein the two folded sections of the contact layer and the facing layer or the backing layer are joined together by a seam;

wherein a material of the facing layer has a higher tensile strength than a material of the contact layer.

20. A method for manufacturing a wound dressing comprising:

providing an absorbent core comprising a top surface and a bottom surface containing a superabsorbent substance;

providing a facing layer;

locating the absorbent core on the facing layer;

folding the facing layer so that the facing layer covers an entire bottom surface of the absorbent core and so that the facing layer comprises two folded sections covering parts of the top surface of the absorbent core;

providing a backing layer;

joining together the facing layer and the backing layer by a seam so that the facing layer and the backing layer form a pouch, wherein the absorbent core is located in the pouch, wherein the seam is at least partly formed between the two folded sections of the facing layer and the backing layer;

providing a contact layer so that it covers the facing layer;

folding the contact layer so that the contact layer comprises two folded sections covering parts of the two folded sections of the facing layer; and joining together the two folded sections of the contact layer and the facing layer by exclusively a first seam between a first of the two folded sections of the facing layer and a first of the two folded sections of the contact layer and a second seam between a second of the two folded sections of the facing layer and a second of the two folded sections of the contact layer.

21. A method for manufacturing a wound dressing comprising:

providing an absorbent core comprising a top surface and a bottom surface containing a superabsorbent substance;

providing a facing layer;

locating the absorbent core on the facing layer;

folding the facing layer so that the facing layer covers an entire bottom surface of the absorbent core and so that the facing layer comprises two folded sections covering parts of the top surface of the absorbent core;

providing a backing layer;

joining together the facing layer and the backing layer by a seam so that the facing layer and the backing layer form a pouch, wherein the absorbent core is located in the pouch, wherein the seam is at least partly formed between the two folded sections of the facing layer and the backing layer;

providing a contact layer so that it covers the facing layer;

folding the contact layer so that the contact layer comprises two folded sections covering parts of the two folded sections of the facing layer; and joining together the two folded sections of the contact layer and the two folded sections of the facing layer and the backing layer by a seam.

22. A method for manufacturing a wound dressing comprising:

providing an absorbent core comprising a top surface and a bottom surface containing a superabsorbent substance;

providing a facing layer;

locating the absorbent core on the facing layer;

folding the facing layer so that the facing layer covers an entire bottom surface of the absorbent core and so that the facing layer comprises two folded sections covering parts of the top surface of the absorbent core;

providing a backing layer;

joining together the facing layer and the backing layer by a seam so that the facing layer and the backing layer form a pouch, wherein the absorbent core is located in the pouch, wherein the seam is at least partly formed between the two folded sections of the facing layer and the backing layer;

providing a contact layer so that it covers the facing layer;

folding the contact layer so that the contact layer comprises two folded sections covering parts of the two folded sections of the facing layer which is smaller than an overall area of the two folded sections of the facing layer;

joining the backing layer directly together with the area of the two folded sections of the facing layer not in engagement with the two folded sections of the contact layer; and joining together the two folded sections of the contact layer and the facing layer or the backing layer by a seam.

23. A method for manufacturing a wound dressing comprising:

providing an absorbent core comprising a top surface and a bottom surface containing a superabsorbent substance;

providing a facing layer;

locating the absorbent core on the facing layer;

folding the facing layer so that the facing layer covers an entire bottom surface of the absorbent core and so that the facing layer comprises two folded sections covering parts of the top surface of the absorbent core;

providing a backing layer;

joining together the facing layer and the backing layer by a seam so that the facing layer and the backing layer form a pouch, wherein the absorbent core is located in the pouch, wherein the seam is at least partly formed between the two folded sections of the facing layer and the backing layer;

providing a contact layer so that it covers the facing layer;

folding the contact layer so that the contact layer comprises two folded sections covering parts of the two folded sections of the facing layer; and joining together the two folded sections of the contact layer and the backing layer by a seam, wherein the contact layer is not joined together with the facing layer.

24. A method for manufacturing a wound dressing comprising:

providing an absorbent core comprising a top surface and a bottom surface containing a superabsorbent substance;

providing a facing layer;

locating the absorbent core on the facing layer;

folding the facing layer so that the facing layer covers an entire bottom surface of the absorbent core and so that the facing layer comprises two folded sections covering parts of the top surface of the absorbent core;

providing a backing layer;

joining together the facing layer and the backing layer by a seam so that the facing layer and the backing layer form a pouch, wherein the absorbent core is located in the pouch, wherein the seam is at least partly formed between the two folded sections of the facing layer and the backing layer;

providing a contact layer so that it covers the facing layer, wherein a material of the facing layer has a higher tensile strength than a material of the contact layer;

folding the contact layer so that the contact layer comprises two folded sections covering parts of the two folded sections of the facing layer; and joining together the two folded sections of the contact layer and the facing layer or the backing layer by a seam.

* * * * *

UNITED STATES PATENT AND TRADEMARK OFFICE
CERTIFICATE OF CORRECTION

PATENT NO. : 10,426,669 B2
APPLICATION NO. : 14/922387
DATED : October 1, 2019
INVENTOR(S) : Rolf Rovaniemi Page 1 of 1

It is certified that error appears in the above-identified patent and that said Letters Patent is hereby corrected as shown below:

On the Title Page

Column 1, Item (73), Assignee "Aborbest AB" should be corrected to --ABSORBEST AB--.

Signed and Sealed this
Twenty-eighth Day of January, 2020

Andrei Iancu
*Director of the United States Patent and Trademark Office*